United States Patent [19]
Deninno et al.

[11] Patent Number: 6,150,336
[45] Date of Patent: Nov. 21, 2000

[54] STEROIDAL GLYCOSIDES

[75] Inventors: Michael P. Deninno, Gales Ferry; Peter A. McCarthy, Pawcatuck, both of Conn.

[73] Assignee: Pfizer Inc., New York, N.Y.

[21] Appl. No.: 08/952,109

[22] PCT Filed: May 29, 1995

[86] PCT No.: PCT/IB95/00409

§ 371 Date: Nov. 21, 1997

§ 102(e) Date: Nov. 21, 1997

[87] PCT Pub. No.: WO96/38466

PCT Pub. Date: Dec. 5, 1996

[51] Int. Cl.[7] ...................... A61K 31/565; A61K 31/575; A61K 31/705
[52] U.S. Cl. .................. 514/26; 536/5; 514/824
[58] Field of Search ........................... 514/26, 824; 536/5

[56] References Cited

U.S. PATENT DOCUMENTS

| | | | |
|---|---|---|---|
| 4,461,762 | 7/1984 | Malinow | 424/182 |
| 4,602,003 | 7/1986 | Malinow | 514/26 |
| 4,602,005 | 7/1986 | Malinow | 514/26 |
| 5,455,335 | 10/1995 | Kahne et al. | 536/5 |
| 5,629,295 | 5/1997 | Deninno et al. | 514/26 |
| 5,698,526 | 12/1997 | Deninno | 514/26 |
| 5,703,052 | 12/1997 | Deninno et al. | 514/26 |

FOREIGN PATENT DOCUMENTS

| | | | |
|---|---|---|---|
| 9307167 | 4/1993 | WIPO | C07J 71/00 |
| 9311150 | 6/1993 | WIPO | C07J 71/00 |
| 9400480 | 1/1994 | WIPO | C07J 71/00 |
| 9425479 | 11/1994 | WIPO | C07J 71/00 |

OTHER PUBLICATIONS

Malinow, M.R., et al., "Effects of α–and β–Tigogenin Cellobiosides on Cholesterol Absorption," *Steroids*, 48/3–4, Sept.–Oct. 1986, pp. 197–211.

Kintia, P.K., et al., *Kim. Pharm. Zh.*, 1981, 15(9), pp. 55–60.

Kintya, P.K., et al., *Kim. Pharm. Zh.*, 1981, 15(9), pp. 55–60. (Russian text).

Kintya, P.K., et al., "Searching for Hypocholesterolemic substances Among the Steroidal Glycosides," pp. 55–60. (translation of Russian text).

*Primary Examiner*—Howard C. Lee
*Attorney, Agent, or Firm*—Peter C. Richardson; Gregg C. Benson; Todd M. Crissey

[57] ABSTRACT

The invention relates to certain steroidal glycoside derivatives useful as hypocholesterolemic agents and anti-atherosclerosis agents. The present invention is also directed to pharmaceutical compositions comprising such derivatives and use of such derivatives in treating hypercholesterolemia or atherosclerosis.

7 Claims, No Drawings

STEROIDAL GLYCOSIDES

CROSS REFERENCE TO RELATED APPLICATION

This application is the national stage of International Application No. PCT/IB95/00409 having an international filing date of May 29, 1995.

BACKGROUND OF THE INVENTION

This invention relates to steroidal glycosides and methods of using the same, particularly as hypocholesterolemic agents and antiatherosclerosis agents, in mammals.

Many known products possessing hypocholesterolemic activity are cross-linked synthetic polymer derivatives. For example, cross-linked, water-insoluble, bile-acid-binding polystyrene-based resins, e.g., Cholestyramine® agents, have a gritty "mouth-feel", and thus have poor palatability. In addition, these resin beads typically have a low in vivo efficiency. Thus, the effective hypocholesterolemic dose of these materials is excessive, typically 18–24 grams of formulated product per day. Other known polymers having hypocholesterolemic activity include the natural product chitosan and chitosan derivatives as described in European Application pub. no. 0212145. However, the effective hypocholesterolemic dose of these materials is also high.

Other known hypercholesterolemia controlling agents include plant extracts such as "alfalfa saponins". However, these plant extracts are of variable composition and contain significant amounts of non-useful chemical substances. Due to the variations in composition, it is difficult to set a standard dosage or predict the impurities present. Thus, such extracts are not well suited for use by humans. Further, purification of these extracts would be expensive. As an alternative, certain synthetically produced, pure "sapogenin-derived" compounds e.g., substances compounded from spirostane, spirostene or sterol-derived compounds depress cholesterol absorption more effectively than alfalfa extracts on a weight basis and thus can be administered in reasonable sized doses. Because the chemical compositions of these substances are known and because they can be synthesized at a high degree of purity, they are suitable for use by any warm-blooded animal, including humans.

However, unless administered in massive amounts, pure sapogenins do not significantly inhibit cholesterol's absorption. It is only when compounded with another moiety that sapogenins have the desired effect. Examples of such sapogenin compounds are compounds of tigogenin and diosgenin, particularly glycosides thereof. P. K. Kintia, Iu. K. Vasilenko, G. M. Gorianu, V. A. Bobeiko, I. V. Suetina, N. E. Mashchenko, Kim. Pharm. Zh., 1981, 15(9), 55 discloses 3-O-(β-D-galactopyranosyl)hecogenin and its use as a hypocholesterolemic agent. U.S. Pat. Nos. 4,602,003 and 4,602,005 disclose certain steroidal glycosides, in particular 3-O-(β-D-glucopyranosyl)tigogenin and 3-O-(β-D-cellobiosyl)tigogenin and their use for the control of hypercholesterolemia. 3-O-(β-D-cellobiosyl)tigogenin has superior hypocholesterolemic activity when compared to, for example, cholestyramine. PCT publication WO 93/07167 discloses several steroidal glycosides in particular 3-O-(5-C-hydroxymethyl-L-arabino-hexopyranosyl)-tigogenin and 3-O-(5-C-hydroxymethyl-L-arabino-hexopyranosyl)-diosgenin and their use in the control of hypercholesterolemia.

Recently, commonly assigned PCT publication WO 93/11150 has disclosed a number of steroidal glycosides including 11-ketotigogenyl-beta-O-cellobioside, hecogenin-beta-O-cellobioside, diosgenin-beta-O-cellobioside and their use as antihypercholesterolemic agents. Also commonly assigned PCT publication WO 94/00480, the disclosure of which is hereby incorporated by reference, discloses a variety of steroidal glycosides and their use as antihypercholesterolemic agents.

Although the hypocholesterolemic compounds described above make a significant contribution to the art there is a continuing search in this field of art for improved hypocholesterolemic pharmaceuticals.

SUMMARY OF THE INVENTION

This invention is directed to steroidal glycosides, particularly spirostanyl glycosides, that are useful as hypocholesterolemic agents and antiatherosclerosis agents. The compounds of this invention have the formula

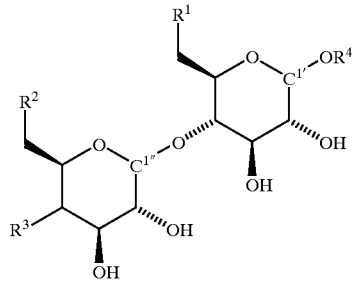

Formula I and the pharmaceutically-acceptable salts and hydrates thereof wherein $R^1$, $R^2$ and $R^3$ are each independently hydrogen, hydroxy, halo, amino, azido, $(C_1-C_6)$alkoxy$(C_1-C_6)$alkoxy or —Z—$R^5$;

Z for each occurence is independently selected from the group consisting of —NH—C(=O)—, —O—C(=O)—, —O—C(=O)—N($R^6$)—, —NH—C(=O)—N($R^6$)—, —O—C(=S)—N($R^6$)— and —O—C(=O)—N($R^6$)—;

$R^6$ for each occurence is independently hydrogen or $(C_1-C_4)$alkyl or $R^6$ is such that when taken together with the nitrogen to which it is attached and with $R^5$, wherein $R^5$ is a covalent bond, it forms pyrrolidinyl, piperidinyl, N-methylpiperazinyl, indolinyl or morpholinyl and such cyclic group may be mono-substituted on carbon with $(C_{1-4})$alkoxycarbonyl;

$R^5$ for each occurence is independently aryl, aryl $(C_1-C_6)$alkyl, $(C_2-C_4)$alkenyl, $(C_1-C_6)$alkyl, $(C_3-C_7)$cycloalkyl or $(C_3-C_7)$cycloalkyl$(C_1-C_6)$alkyl; each $R^5$ optionally mono-, di- or tri-substituted independently with halo, $(C_1-C_4)$alkyl, hydroxy, phenoxy, trifluoromethyl, nitro, $(C_1-C_4)$alkoxy, methylenedioxy, oxo, $(C_1-C_4)$alkylsulfanyl, $(C_1-C_4)$alkylsulfinyl, $(C_1-C_4)$alkylsulfonyl, dimethylamino, mono- or di-$(C_1-C_4)$alkylaminocarbonyl, $(C_1-C_4)$alkylcarbonyl, $(C_1-C_4)$alkoxycarbonyl or pyrrolidinylcarbonyl;

(A)

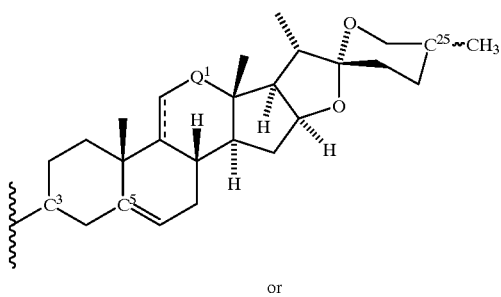

or (B)

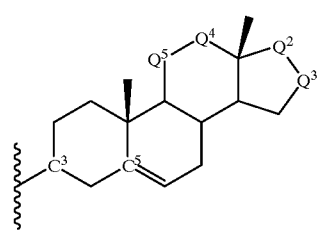

where - - - - - is optionally a double bond, $Q^1$ is C=O and there is a double bond between $C^9$-$C^{11}$, or $Q^1$ is —C(=O)—NH—, —CH(NHR$^7$)—, —CF$_2$—, or

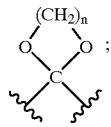

$R^7$ is $R^8$—C(=O)—, $R^8$—S(=O)$_2$— or $R^8$—O—C(=O)—;
n is 2, 3 or 4;
$R^8$ is (C$_1$-C$_6$)alkyl or aryl optionally mono- or di-substituted with halo;
$Q^2$ is —C(=O)—, —CH$_2$—, —C(=N—OR$^9$)— or —CH(CH(CH$_3$)—CH$_2$—CH$_2$—C(=O)(OR$^9$))—;
$R^9$ is (C$_{1-4}$)alkyl or aryl(C$_1$-C$_6$)alkyl;
$Q^3$ is —C(=O)—, —CH$_2$— or

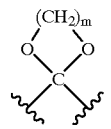

where m is 2, 3 or 4;
or $Q^2$ and $Q^3$, are taken together with the carbon atoms to which they are attached, form

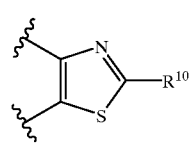

$Q^4$ is —CH$_2$— or —C(=O)—; and $Q^5$ is —CH$_2$— or —C(=O)—;

wherein aryl is carbon-linked and is phenyl, furyl, thienyl, pyrrolyl, oxazolyl, isoxazoyl, oxadiazolyl, thiazolyl, isothiazolyl, benzothiazolyl, thiadiazolyl, pyrazolyl, imidazolyl or pyridyl;

provided that when $Q^2$ is —C(=N—NR$^9$)— then $Q^3$ is not —C(=O)—.

A first group of preferred compounds of Formula I are those compounds wherein $R^1$, $R^2$, and $R^3$ are as defined hereinabove, $R^4$ is the moiety of formula (A) where $Q^1$ is as defined above, the $C^{25}$ is in the (R) conformation, the $C^5$ hydrogen is alpha and the $C^3$ oxy is beta. Especially preferred within this group are compounds wherein the $C^{1'}$ and $C^{1''}$ anomeric oxy are beta and $R^3$ is alpha. Particularly preferred compounds within this especially preferred group are compounds wherein $R^1$ is hydroxy, $R^2$ and $R^3$ are each independently Z—$R^5$ where Z is —O—(C=O)—N(R$^6$)— and $R^6$ is hydrogen.

A second group of preferred compounds of Formula I are those compounds wherein $R^1$, $R^2$, and $R^3$ are as defined hereinabove, $R^4$ is the moiety of formula (B), the $C^3$ oxy is beta, and the $C^5$ hydrogen is alpha. Especially preferred within this group are compounds wherein the $C^{1'}$ and $C^{1''}$ anomeric oxy are beta, and $R^3$ is alpha. Particularly preferred compounds within this especially preferred group are compounds wherein $R^1$ is hydroxy, $R^2$ and $R^3$ are each independently Z—$R^5$ where Z is —O—(C=O)—N(R$^6$)— and $R^6$ is hydrogen.

Yet another aspect of this invention is directed to a method for treating hypercholesterolemia or atherosclerosis in a mammal by administering to a mammal suffering from hypercholesterolemia or atherosclerosis a hypercholesterolemia or atherosclerosis treating amount of a Formula I compound.

This invention is also directed to pharmaceutical compositions for the treatment of hypercholesterolemia or atherosclerosis in a mammal which comprise a compound of the Formula I and a pharmaceutically acceptable carrier.

The compounds of Formula I are herein defined as the single enantiomer having the absolute stereochemistry depicted in Formula I.

By halo is meant chloro, bromo, iodo, or fluoro.

By alkyl is meant straight chain or branched saturated hydrocarbon.

The Z moieties described above are herein defined such that they are to be read from left to right (i.e., the left or first atom is attached to the sugar molecule and not to $R^5$).

Other features and advantages will be apparent from the specification and claims which describe the invention.

DETAILED DESCRIPTION OF THE INVENTION
SCHEME I
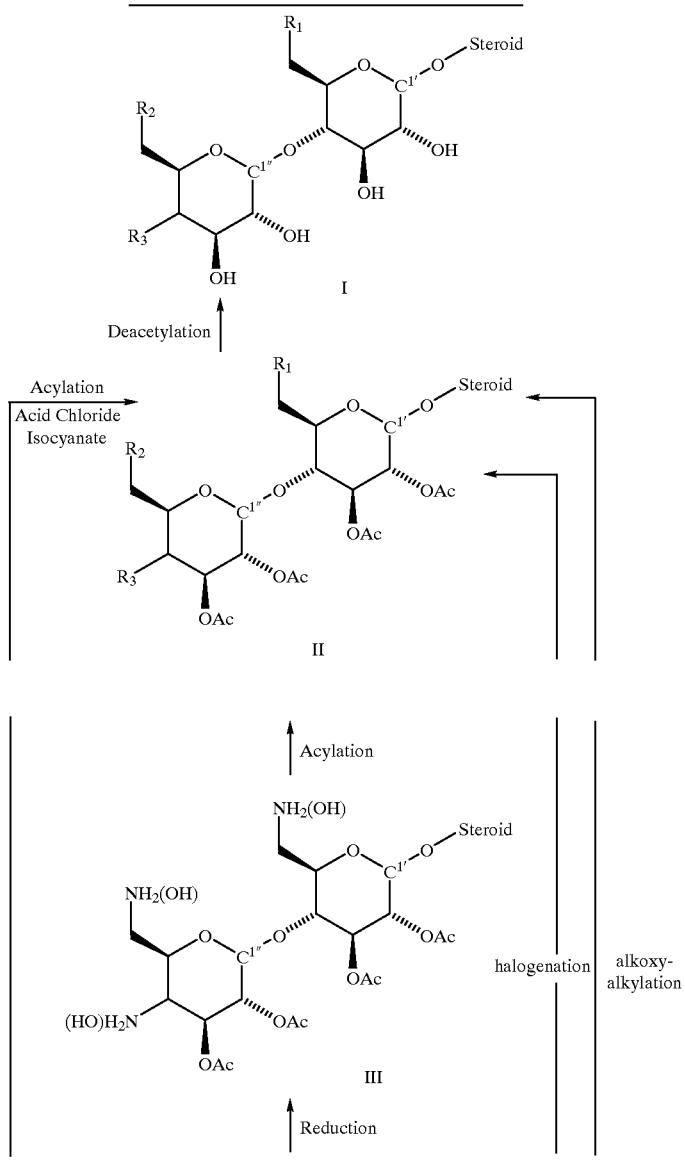

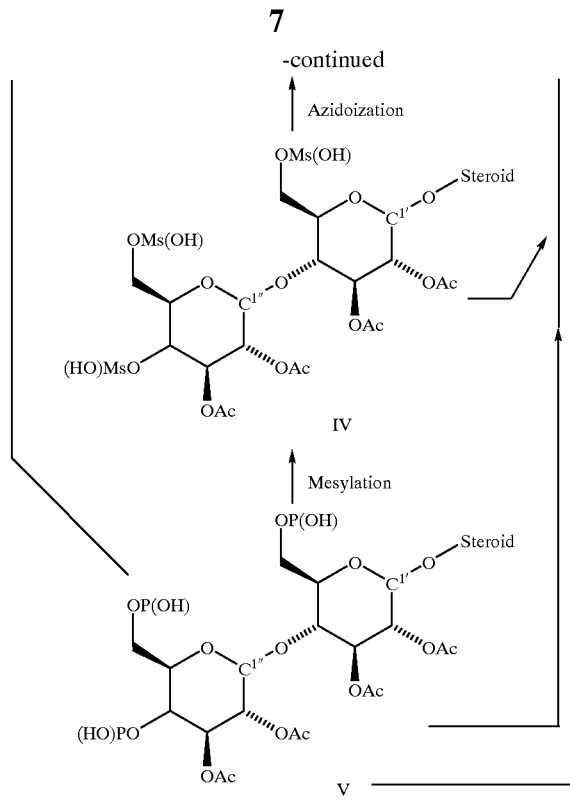

SCHEME II

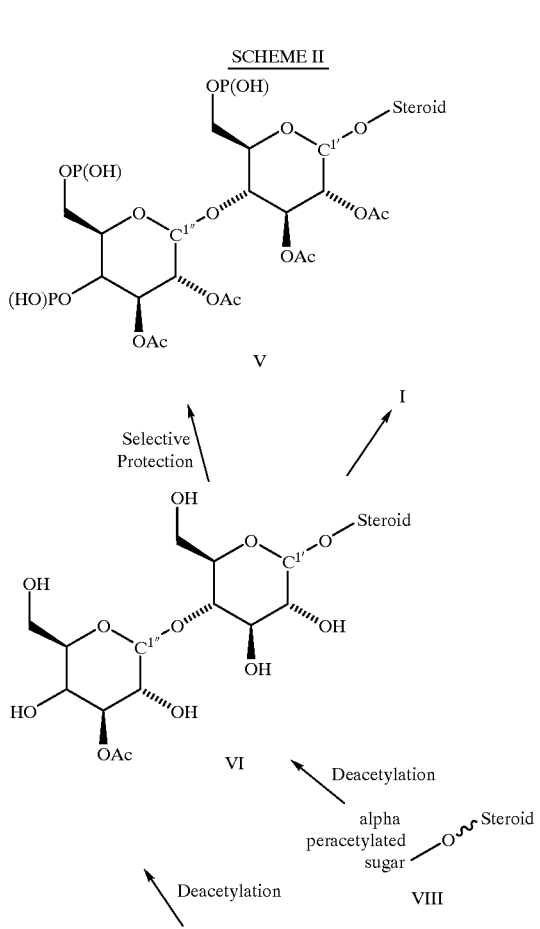

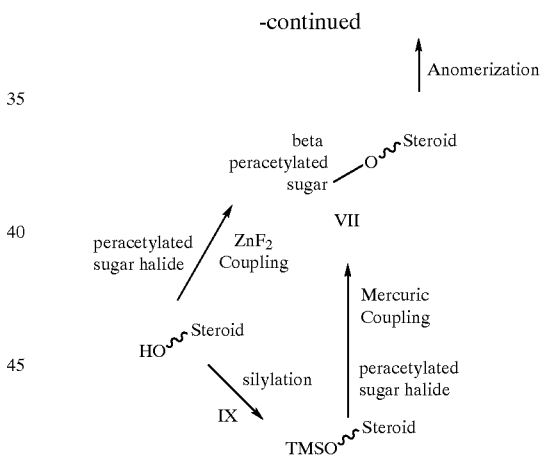

In general the compounds of this invention may be made by coupling the desired protected sugar halide and steroid followed by deprotection. The desired functionality/substituents are attached (following optional selective protection) and a final deprotection is performed. The following text (which is keyed to the above Schemes) provides a more detailed description.

According to reaction Scheme I, the desired Formula I compounds wherein Steroid is the steroidal moiety of the Formula I compound shown above (i.e., wherein $R^4$ is a moiety of formula (A) or (B) and $Q^1, Q^2, Q^3, Q^4, Q^5, C^3, C^5, C^{25}$ are as defined above) and $C^{1'}, C^{1''}, R^1, R^2$ and $R^3$ are as defined above may be prepared by deprotecting (e.g., deacetylating) the appropriate Formula II compound wherein Steroid is the steroidal moiety described above, $C^{1'}$ and $C^{1''}$ are as defined above and $R^1, R^2$, and $R^3$ are as defined above or each independently is a conventionally protected hydroxyl group such as —OAc.

Typically the deprotection (preferably the deacetylation), is accomplished by combining the Formula II compound with a nucleophilic base such as sodium methoxide or potassium cyanide in a polar solvent such as methanol, tetrahydrofuran, n-propanol or mixtures thereof at temperatures of about 0 °C. to about 100° C. (typically at ambient temperatures) and pressures of about 0.5 psi to about 50 psi (typically ambient) for about 0.25 hour to about 2 hours.

Additionally, the compounds may contain a silyl protecting group which can be removed by treating the deacylated product from above with a quaternary ammonium fluoride such as tetrabutyl ammonium fluoride in an anhydrous solvent such as tetrahydrofuran at temperatures of about 0° C. to about 50° C. (typically at ambient temperatures) for about 0.1 to about 3 hours.

The desired Formula II compounds wherein Steroid is the steroid moiety of Formula (A) or (B) shown above (i.e., wherein $Q^1$, $Q^2$, $Q^3$, $Q^4$, $Q^5$, $C^3$, $C^5$, $C^{25}$ are as defined above) and $C^{1'}$ and $C^{1''}$ are as defined above and at least one of $R^1$, $R^2$ and $R^3$ is hydrogen can be prepared by reduction of the corresponding halogenated compound. Typically, the reduction can be performed by treating the halogenated compound (Br and I preferred) with a reducing agent such as tri-n-butyl tin hydride and a radical initiator such as azoisobutylnitrile (AIBN) in an anhydrous aprotic solvent such as toluene at reflux temperature for about 1 hour to about 5 hours.

The desired Formula II compounds wherein Steroid is the steroidal moiety described above, $C^{1'}$ and $C^{1''}$ are as described above and at least one of $R^1$, $R^2$ and $R^3$ is halogen may be prepared by halogenation of the appropriately protected Formula V compound wherein Steroid is the steroidal moiety described above, $C^{1'}$ and $C^{1''}$ are as defined above and $R^1$, $R^2$, and $R^3$ are each independently hydroxy or a conventionally protected hydroxyl group such as —OAc.

Generally the halogenation can be performed by first preparing an appropriately activated and protected form of the Formula V compound (e.g., the Formula IV mesylate) followed by treatment with the desired lithium halide. Typically the mesylation can be performed by combining the Formula V compound and mesyl chloride in the presence of a base, preferably an amine base such as triethylamine and a catalytic amount of a catalyst such as dimethylaminopyridine in an aprotic, anhydrous solvent such as anhydrous dichloromethane at a temperature of about –20° C. to about 20° C. for about one hour to about four hours. The resulting mesylate is then treated with the appropriate lithium halide in a polar solvent such as N,N-dimethylformamide at a temperature of about 70° C. to about 100° C. for about one to about three hours.

Alternatively, iodination can be performed by combining iodine and the appropriate Formula V compound in an anhydrous aprotic solvent such as toluene (in the presence of imidazole and triphenylphosphine) under reflux conditions and ambient pressure for about four to about eight hours.

Alternatively, the fluorination can be performed by combining the appropriate Formula V compounds with a fluorinating agent such as dialkylaminosulfur trifluoride (e.g., DAST) in an anhydrous, aprotic solvent such as dimethoxy ethane or dichloroethane at a temperature of about –10° C. to about 10° C. and then, after about twenty minutes to about two hours, raising the temperature to about 30° C. to about 60° C. for about one hour to about four hours.

Alternatively, a selective bromination (i.e., $R^2$=Br) can be accomplished by treating the appropriate Formula V compound (wherein $C^{6''}$ and $C^{4''}$ are substituted with OH and $C^{6'}$ is substituted with a conventionally protected hydroxyl group such as —OAc) with carbon tetrabromide and triphenyl phosphine and an amine base such as pyridine in an anhydrous aprotic solvent such as dichloromethane at ambient temperature for about 6 hours to about 48 hours.

The desired Formula II compounds wherein Steroid is the steroidal moiety described above, $C^{1'}$ and $C^{1''}$ are as described above and at least one of $R^1$, $R^2$ and $R^3$ is $(C^1-C^6)$alkoxy$(C^1-C^6)$alkoxy may be prepared by alkylating the appropriately protected Formula V compound wherein Steroid is the steroidal moiety described above, $C^{1'}$ and $C^{1''}$ are as defined above and $C^{6'}$, $C^{6''}$ and $C^{4''}$ are each independently substituted with hydroxy or a conventionally protected hydroxyl group such as —OAc.

Typically, the appropriate Formula V compound is combined with an excess of the appropriate alkoxyalkyl halide and a trialkyl amine base such as diisopropylethylamine in the presence of an anhydrous, aprotic solvent such as dichloroethane at a temperature of about 15° C. to about 35° C. (typically ambient temperature) for about one to about eight hours followed by mixing for one to four hours at a temperature of about 40° C. to about 70° C.

The desired Formula II compounds wherein Steroid is the steroid moiety described above and $C^{1'}$ and $C^{1''}$ are as defined above and at least one of $R^1$, $R^2$, and $R^3$ is Z—$R^5$ and $R^5$ contains a ketone group can be prepared by oxidation of the corresponding hydroxy substituted Formula II compound. Typically the oxidation is performed by treating the hydroxy compound with an oxidizing agent, such as pyridinium chlorochromate, in an anhydrous halogenated solvent such as dichloromethane at 0° C. to about 30° C., generally at ambient temperatures, for about 2 hours to about 24 hours.

Similarly, Formula II compounds described in the above paragraph wherein $R^5$ contains an alkylsulfinyl group may be prepared by oxidation of the corresponding alkylsulfanyl substituted Formula II compound. Typically the appropriate Formula II compound is treated with one equivalent of a peroxy acid such as metachloroperbenzoic acid in an anhydrous halogenated solvent such as dichloromethane at ambient temperature for 1 hour to about 6 hours. The corresponding alkylsulfonyl Formula II compounds can be prepared in an analogous manner using excess peroxy acid.

The desired Formula II compounds wherein Steroid is the steroid moiety described above, and $C^{1'}$ and $C^{1''}$ are as defined above and at least one of $R^1$, $R^2$, and $R^3$ is Z—$R^5$ and $R^5$ is alkylaminocarbonylalkyl can be prepared from the corresponding carboxy alkyl Formula II compounds through an amide forming reaction. Typically the amide is formed by reacting the carboxylic acid with a carboxyl activating agent such as a substituted carbodiimide and hydroxybenzotriazole and a primary or secondary amine chosen to give the desired amide product. The reaction is typically performed in an anhydrous aprotic solvent such as dichloromethane at ambient temperature for about 0.5 hours to about 6 hours. The carboxy alkyl Formula II compounds used in this procedure are typically prepared from the corresponding benzyl ester (the preparation of the benzyl ester being described herein) by a hydrogenolysis reaction. Thus the ester is treated with a hydrogenation catalyst such as palladium on carbon in an alcoholic solvent such as methanol and placed under 1 to 4 atmospheres of hydrogen, typically 2 atmospheres, for about 0.5 to about 8 hours.

The desired Formula I compounds wherein Steroid is the steroidal moiety described above, $C^{1'}$ and $C^{1''}$ are as described above and at least one of $R^1$, $R^2$ and $R^3$ is —O—C(=O)—$R^5$ or —O—C(=O)—N($R^6$)—$R^5$ may be prepared by acylating the appropriate Formula VI compound wherein $Q^1$, $Q^2$, $Q^3$, $Q^4$, $Q^5$, $C^3$, $C^5$, $C^{25}$, $C^{1'}$ and $C^{1''}$ are as defined above (See Scheme II). Alternatively, the desired Formula II compounds wherein at least one of $R^1$, $R^2$ and $R^3$ is —O—C(=O)—$R^5$, —O—C(=O)—N($R^6$)—$R^5$ or —O—C(=S)—N($R^6$)—$R^5$ may be prepared by acylating the appropriately protected Formula V compound wherein Steroid is the steroidal moiety described above, $C^{1'}$ and $C^{1''}$ are as defined above and $C^{6'}$, $C^{6''}$ and $C^{4''}$ are each independently substituted with hydroxy or a conventionally protected hydroxyl group such as —OAc (See Scheme I).

A nonselective mixture of ester and carbamoyloxy substitution at $R^1$ and $R^2$ is achieved by treating the appropriately protected perhydroxy sugar Formula VI compound with the appropriate acid chloride or isocyanate and an amine base that also acts as an anhydrous solvent such as pyridine in the presence of a drying agent such as molecular sieves at a temperature of about −60° C. to about 25° C. for about 5 minutes to about 24 hours while the reaction is allowed to warm to ambient temperature. Different products and product mixes result from the variation of the amount of acid chloride or isocyanate used, the length of reaction time and the reactivity of the acid chloride or isocyanate.

Alternatively, a more selective acylation is performed by treating the appropriately protected (e.g., OAc) steroidal glycoside Formula V compound with the appropriate isocyanate or acid chloride in the presence of a base, preferably an amine base such as triethylamine or pyridine and a catalytic amount of an acylation catalyst such as dimethylaminopyridine in an anhydrous, aprotic solvent such as dichloromethane at a temperature of about −20° C. to about 20° C. The reaction mixture is allowed to warm to ambient temperature for about 10 minutes to about two hours. The carbamoylation can also be achieved by treating the appropriately protected Formula V compound with the appropriate isocyanate in the presence of cuprous chloride in a polar aprotic solvent such as dimethyl formamide at ambient temperature for 2 hours to about 10 hours.

The carbamoylation may also be achieved by treating the appropriately protected Formula V compound with the appropriate isocyanate in the presence of an organotin catalyst such as dibutyl tin dilaurate in an anhydrous aprotic solvent such as dichloromethane at ambient temperature for about 2 hours to about 24 hours.

In addition, the desired Formula II compounds wherein at least one of $R^1$, $R^2$ and $R^3$ is a carbamoyloxy or thiocarbamoyloxy moiety may be prepared by treatment of the appropriately protected (e.g., OAc) steroidal glycoside Formula V compound with a phosgene equivalent such as carbonyl diimidazole or a thio-phosgene equivalent such as thiocarbonyl diimidazole in the presence of a base, preferably an amine base such as diisopropylethylamine in an aprotic, anhydrous solvent such as dichloroethane at a temperature of about 15° C. to about 30° C. (typically ambient temperature) for about one to about four hours. The appropriate amine is added and the reaction mixture is stirred at the same temperature for about one hour to about six hours, and heated if necessary to about 40° C. to about 60° C. for about one to about four hours.

The desired Formula II compounds wherein Steroid is the steroidal moiety described above, $C^{1'}$ and $C^{1''}$ are as described above and at least one of $R^1$, $R^2$ and $R^3$ is —NH—C(=O)—$R^5$ or —NH—C(=O)—N($R^6$)—$R^5$ may be prepared by acylating the appropriately protected Formula III compound wherein Steroid is the steroidal moiety described above, $C^{1'}$ and $C^{1''}$ are as defined above and at least one of $R^1$, $R^2$, and $R^3$ is amino.

Typically the amide may be prepared by the treatment of the appropriately protected (e.g., OAc) steroidal glycosidyl amine with the appropriate acid anhydride or acid chloride in the presence of a base, preferable an amine base such as triethylamine in an anhydrous, aprotic solvent such as dichloromethane for about one to about three hours at a temperature of about 0° C. to about 25° C.

Alternatively, the ureas may be prepared by the treatment of the appropriately protected (e.g., OAc) steroidal glycosidyl amine with the appropriate isocyanate in an anhydrous, aprotic solvent such as dichloromethane for about one to about three hours at a temperature of about 0° C. to about 25° C.

The desired Formula III compound (which happens in this case to be a Formula II compound) wherein Steroid is the steroidal moiety described above, $C^{1'}$ and $C^{1''}$ are as defined above and at least one of $R^1$, $R^2$, and $R^3$ is amino or azido may be prepared from the corresponding Formula IV mesylated or halogenated compounds by azide displacement followed if necessary by reduction.

Typically the mesylate compound is exposed to a metal azide such as sodium azide in a polar, aprotic solvent such as N,N-dimethylformamide (in an inert atmosphere) at a temperature of about 70° C. to about 150° C. for about 2 to about 10 hours. The preparation of such mesylate compounds are described above for the lithium halide halogenation. Typically the azido compounds are reduced to the corresponding amines by exposure to hydrogen gas in the presence of a noble metal catalyst such as palladium on carbon at ambient temperature for about four to about forty-eight hours, under pressures of about one to about three atmospheres.

The desired Formula V compound (appropriately protected to yield the desired substitution described above) wherein Steroid is the steroidal moiety described above, $C^{1'}$ and $C^{1''}$ are as defined above and $C^{6''}$, $C^{6'}$ and $C^{4''}$ are each independently substituted with hydroxy or a conventionally protected hydroxyl group such as —OAc may be prepared by conventional protecting group methods of organic synthesis known to those skilled in the art from the corresponding Formula VI compounds wherein $Q^1$, $Q^2$, $Q^3$, $Q^4$, $Q^5$, $C^3$, $C^5$, $C^{25}$, $C^{1'}$ and $C^{1''}$ are as defined above. For a general description of protecting groups and their use, see T. W. Greene, *Protective Groups in Organic Synthesis,* John Wiley & Sons, New York, 1991. In addition, as an aid to the preparation of the above protected steroidal glycosides, the following paragraphs describe the preparation of various protected steroidal glycosides from their hydroxy analogues using a combination of differentially selective protecting groups and sequential protection reactions.

For example, the desired Formula V compound wherein Steroid is the steroidal moiety described above, $C^{1'}$ and $C^{1''}$ are as defined above, $C^{6''}$ and $C^{6'}$ are substituted with hydroxy and $C^{4''}$ is substituted with OP where P is an acyl protecting group may be conveniently prepared from the corresponding perhydroxy steroidal glycoside by silylation, acylation and desilylation. The appropriate Formula VI compound is reacted with a base, preferably an amine base such as imidazole, a bulky silylating agent selected to afford the desired silyl protecting group defined above, such as a trisubstituted silylhalide, preferably t-butyldiphenylsilyl chloride and a catalytic amount of a silylation catalyst such as dimethylaminopyridine in an anhydrous, aprotic solvent such as N, N-dimethyl-formamide at about −20° C. to about 10° C. followed by ambient temperature stirring for about one to about six hours. Upon completion of the silylation, a base, preferably an amine base such as pyridine and an acylating agent selected to afford the desired acyl protecting group defined above such as acetic anhydride are added at ambient temperature and pressure for about three to about twelve hours to achieve acetylation to prepare the desired protected compound (e.g., Formula IIB compound). The resulting product is treated with hydrogen fluoride in an anhydrous, aprotic solvent such as pyridine at about −20° C. to about 10° C. followed by ambient temperature stirring for about two to about six hours to prepare the desired selectively protected compound (e.g., Formula IIA compound). This product contains hydroxyl groups at the $C^{6'}$ and $C^{6''}$ positions which can be further differentiated by reaction with one equivalent of a protecting group such as acetic anhydride in the presence of a base, such as pyridine at ambient temperatures for about 1 to about 4 hours. This procedure gives a mixture of Formula V compounds which contain a single hydroxyl group at either the $C^{6'}$ or the $C^{6''}$ position which can be separated chromatographically.

In addition, the desired Formula V compound wherein Steroid is the steroidal moiety described above, $C^{1'}$ and $C^{1''}$ are as defined above, $C^{6''}$ and $C^{4''}$ are substituted with hydroxy and $C^{6'}$ is substituted with OP where P is an acyl protecting group may be conveniently prepared from the corresponding perhydroxy steroidal glycoside by ketalization, acylation and deketalization. The appropriate Formula VI compound is reacted with an acetal or ketal selected to afford the desired cyclic protecting group defined above, such as benzaldehyde dimethyl acetal or anisaldehyde dimethyl acetal, in the presence of a catalytic amount of a strong acid such as camphorsulfonic acid in an anhydrous, aprotic solvent such as chloroform or dichloroethane under reflux conditions for about two to about six hours at ambient pressure. Upon completion of the ketalization, a base preferably an amine base such as pyridine, a catalytic amount of an acylation catalyst such as dimethylaminopyridine and an acylating agent selected to afford the desired acyl protecting group defined above such as acetic anhydride or chloroacetic anhydride were added at a temperature of about −20° C. to about 10° C. followed by ambient temperature stirring for about one to about twelve hours to prepare the desired protected compound (e.g., Formula IIC compound). The resulting product is treated with 80% acetic acid in water at about 50° C. to about reflux conditions for about one to about four hours or with trifluoroacetic acid in a mixture of dichloromethane and methanol at ambient temperature for about two hours to about eight hours to prepare the desired protected compound (e.g., Formula IIA compound).

This product can further be converted to the Formula V compound wherein $C^{6'}$ and $C^{6''}$ are substituted with OP where P is an acyl or silyl protecting group and $C^{4''}$ is substituted with OH by a selective silylation reaction. Typically the silylation is performed by treating the appropriate Formula V compound wherein $C^{4''}$ and $C^{6''}$ are substituted with OH and $C^{6'}$ is substituted with OP where P is an acyl protecting group with a silylating agent such as tert-butyidimethylsilyl chloride and a base preferably an amine base such as imidazole in a polar aprotic solvent such as dimethyl formamide at ambient temperature for about 12 hours to about 48 hours.

The desired Formula V compound wherein Steroid is the steroidal moiety described above, $C^{1'}$ and $C^{1''}$ are as defined above, $C^{6''}$ and $C^{4''}$ are substituted with hydroxy and $C^{6'}$ is substituted with OP where P is an ether protecting group may be conveniently prepared from the corresponding perhydroxy steroidal glycoside by ketalization, etherification and deketalization. The ketalization is performed as described above. Upon completion, the solvent is removed and replaced with a polar aprotic solvent such as dimethyl formamide. The appropriate alkyl halide is added such as benzyl bromide, followed by a strong base such as sodium hydride at a temperature of about −20° C. to about 0° C. for about 1 hour to about 12 hours. The deketalization is performed as described above.

The desired Formula VI compounds wherein $Q^1$, $Q^2$, $Q^3$, $Q^4$, $Q^5$, $C^3$, $C^5$, $C^{25}$, $C^{1'}$ and $C^{1''}$ are as defined above may be prepared from the corresponding Formula VII or Formula VIII peracetylated steroidal glycoside by the deacetylation process described above. For those Formula VI compounds wherein the $C^{1'}$ anomeric oxy is alpha an anomerization is performed on the corresponding Formula VII compound wherein the $C^{1'}$ anomeric oxy is beta prior to deacetylation. The stereochemical terms alpha and beta refer to the configuration of the attachment carbon of the sugar. Typically the anomerization is performed by treatment with a mineral acid such as hydrobromic acid in an anhydrous aprotic solvent such as methylene chloride at temperatures of about 20° C. to about 40° C. (typically ambient) for at least 24 hours, typically to several days.

The Formula VII compounds wherein the steroid moiety $R^4$ is (B), $Q^2$ is —C(=N—OR$^9$)— and $Q^3$, $Q^4$ and $Q^5$ are methylene are prepared from the corresponding Formula VII compound wherein $Q^2$ is carbonyl and $Q^3$ is methylene. Thus, the appropriate Formula VII compound is reacted with a substituted hydroxyl amine, such as O—benzylhydroxyl amine, in the presence of a base, preferably an amine base such as pyridine in polar solvent such as methanol at ambient temperature for about 1 hour to about 6 hours.

The Formula VII compounds wherein the steroid moiety $R^4$ is (A), $Q^1$ is —C(=O)NH— and $C^3$, $C^5$ and $C^{25}$ are as defined above are prepared from the corresponding Formula VII compound wherein $Q^1$ is carbonyl. Thus the appropriate Formula VII compound is reacted with hydroxyl amine hydrochloride in the presence of a base, preferably an amine base such as pyridine in polar solvent such as methanol at ambient temperature for about 6 hour to about 24 hours. The resultant oxime is treated with p-toluenesulfonyl chloride in the presence of a base, preferably an amine base such as pyridine which also acts as solvent, and an acylation catalyst such as dimethyl amino pyridine at ambient temperature for about 12 to about 48 hours.

The desired Formula VII compounds wherein $Q^1$, $Q^2$, $Q^3$, $Q^4$, $Q^5$, $C^3$, $C^5$ and $C^{25}$ are as described above may be prepared by coupling the appropriate acetylated sugar halide (e.g., bromide) and steroid. A zinc fluoride promoted coupling of the appropriate Formula IX compound (wherein $Q^1$, $Q^2$, $Q^3$, $Q^4$, $Q^5$, $C^3$, $C^5$ and $C^{25}$ are as described above) and peracetylated sugar halide is used and, in select cases, a mercuric bromide and mercuric cyanide promoted coupling of the appropriate Formula X compound (e.g., trimethyl silyl ether of the Formula IX compound wherein $Q^1$, $Q^2$, $Q^3$, $Q^4$, $Q^5$, $C^3$, $C^5$ and $C^{25}$ are as described above and peracetylated sugar halide is used. The appropriate coupling method for any particular example is known to those of ordinary skill in the art in view of the disclosure.

Generally, the zinc fluoride promoted coupling of the Formula IX compound and the peracetylated sugar bromide occurs in a non-protic, anhydrous reaction-inert solvent (e.g., acetonitrile) at a temperature of about 20° C. to about 100° C. for about 0.5 to about 12 hours. Typically about 0.5 to about 4 equivalents (based on Formula IX compound) zinc fluoride is used and about 0.5 to about 3 equivalents acetylated sugar bromide is used. Preferably the coupling is acid catalyzed and it is especially preferred that hydrohalic acid generated during the reaction is used as the acid catalyst. The desired compounds may be prepared at pressures of 0.5 to 50 psi, although typically ambient pressures are used. In a preferred isolation technique the glycosides may be precipitated from the crude filtered reaction mixture (e.g., acetonitrile product solution) by the addition of about 25% to 75% water and the remainder alcohol (e.g., methanol). Precipitation of the product from aqueous methanol/acetonitrile requires less processing than an extractive isolation, and provides a product of greater purity.

Generally, the mercuric bromide and mercuric cyanide promoted coupling of the Formula X compound and the acetylated sugar bromide is performed in an aprotic, anhydrous solvent such as methylene chloride at a temperature of about 20° C. to about 100° C. for about 0.5 to about 6 hours. Typically about 0.5 to about 4 equivalents (based on acetylated sugar bromide) mercuric bromide and mercuric cyanide is used and about 0.5 to about 3 equivalents peracetylated sugar bromide is used. The desired compounds may be prepared at pressures of 0.5 to 50 psi, although typically ambient pressures are used. Preferably they are isolated as described for the zinc fluoride promoted coupling of the Formula IX compound.

The desired Formula X compounds wherein $Q^1$, $Q^2$, $Q^3$, $Q^4$, $Q^5$, $C^3$, $C^5$ and $C^{25}$ are as described above may be prepared by silylating the appropriate Formula IX compound wherein $Q^1$, $Q^2$, $Q^3$, $Q^4$, $Q^5$, $C^3$, $C^5$ and $C^{25}$ are as described above. Generally the Formula IX compound, a base such as triethylamine and an activated trialkylsilyl compound (e.g., trimethylsilyl trifluoromethane sulfonate of trimethylsilyl chloride) are reacted in an aprotic, anhydrous solvent such as methylene chloride at a temperature less than about 10° C. for about 0.5 hour to about two hours.

In general, the procedures described above may be combined thus providing Formula I compounds wherein the $R^1$, $R^2$ and/or $R^3$ groups are dissimilar (e.g. halogenation followed by carbamoylation).

The starting materials and/or reagents for the above described reaction schemes (e.g., alkoxyalkyl halide, acid anhydride, peracetylated sugar halides, acid chlorides, isocyanates, steroids, amines, trialkylsilylchlorides, carbonyl diimidazoles, thiocarbonyl diimidazoles, silylating agents, acid derivatives, acetals, ketals, protecting groups) are readily available or can be easily synthesized by those of ordinary skill in the art using conventional methods of organic synthesis. For example some of the compounds of this invention require the synthesis of substituted amines and carboxylic acids which eventually will become $R^5$ groups. Such preparations are standard and known to those of ordinary skill in the art.

In addition, as an aid to the preparation of the above steroids, the following paragraphs describe the preparation of the various Formula IX compounds. Literature references for the preparation of Formula IX steroid compounds (wherein the steroid moiety $R^4$ is (A), $Q^1$ and the stereochemistry of the $C^5$ hydrogen (or lack of the $C^5$ hydrogen) and $C^{25}$ carbon are as defined below) are described in Tables I and II.

TABLE I

| Formula IX Compounds Where the $C^3$ Hydroxy Group is Beta | | | |
|---|---|---|---|
| $C^5$ hydrogen | $C^{25}$ | $Q^1$ | Reference |
| α | R | C=O | Marker et. al., J. Am. Chem. Soc. (1947) 69, 2167. |
| α | S | C=O | Callow & James, J. Chem. Soc. (1955) 1671. |

TABLE I-continued

| Formula IX Compounds Where the $C^3$ Hydroxy Group is Beta | | | |
|---|---|---|---|
| $C^5$ hydrogen | $C^{25}$ | $Q^1$ | Reference |
| β | R | C=O | Marker et. al., J. Am. Chem. Soc. (1947) 69, 2167. |
| β | S | C=O | Kenney & Wall J. Org. Chem. (1957) 22, 468. |

TABLE II

| Formula IX Compounds Where the $C^3$ Hydroxy Group is Beta and There is a Double Bond Between $C^5$-$C^6$ | | |
|---|---|---|
| $C^{25}$ | $Q^1$ | Reference |
| R | C=O | Walens, et al., J. Org. Chem. (1957) 22, 182. |
| S | C=O | Walens, et al., J. Org. Chem. (1957) 22, 182. |

The following paragraphs describe and/or give literature references for the preparation of the various steroids used as starting materials. The Formula IX compounds wherein the steroid moiety $R^4$ is (A), $Q^1$ is —$CF_2$— are prepared from the corresponding Formula IX compounds wherein $Q^1$ is carbonyl and the configuration at $C^3$, $C^5$ and $C^{25}$ are set by using the appropriate starting material in Table 1 or 2. In general, the $C^3$ hydroxyl group of the spirostane is protected as the corresponding acetate and the compound is treated with a fluorinating agent such as diethyl amino sulfur trifluoride in an anhydrous, non-protic solvent such as dichloroethane or dimethoxy ethane at reflux temperature for about 12 hours to about 48 hours. The acetate is then removed by treatment with a nucleophilic base such as sodium methoxide in a mixture of methanol and tetrahydrofuran at ambient temperature for about 1 hour to about 6 hours.

The Formula IX compounds wherein the steroid moiety $R^4$ is (A), $Q^1$ is

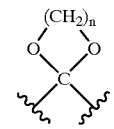

are prepared from the corresponding Formula IX compounds wherein $Q^1$ is carbonyl and the configuration at $C^3$, $C^5$ and $C^{25}$ are set by using the appropriate starting material in Table 1 or 2. In general, the $C^3$ hydroxyl group of the spirostane is protected as the corresponding acetate and treated with the appropriate alkane diol under a Lewis acid catalysis such as boron trifluoride in an anhydrous, aprotic solvent such as dichloromethane at ambient temperature for about 24 hours to about 72 hours. The acetate protecting group is then removed as described above.

The Formula IX compounds wherein the steroid moiety $R^4$ is (A), $Q^1$ is —CH(NHR$^7$)— are prepared from the corresponding Formula IX compounds wherein $Q^1$ is carbonyl and the configuration at $C^3$, $C^5$ and $C^{25}$ are set by using the appropriate starting material in Table 1 or 2. In general, the spirostane is reductively aminated using ammonium acetate in the presence of a reducing agent such as sodium cyano borohydride, in a polar solvent such as methanol at ambient temperature for about 6 hours to about 24 hours. This amine compound is treated with an acid chloride, isocyanate or sulfonyl chloride in the presence of a base, preferably an amine base such as pyridine in an aprotic solvent such as dichloromethane for about 1 to about 12 hours to prepare the desired Formula IX compound.

The Formula IX compounds wherein the steroid moiety $R^4$ is (A), $Q^1$ is carbonyl and there is a double bond between $C^9$ and $C^{11}$ are prepared from the corresponding Formula IX compounds wherein $Q^1$ is carbonyl, the bond between $C^9$ and $C^{11}$ is a single bond, and the configuration at $C^3$, $C^5$ and $C^{25}$ are set by using the appropriate starting material in Table 1 or 2. In general, the $C^3$ hydroxyl group of the spirostane is protected as the corresponding acetate and then treated with an oxidizing agent such as selenium dioxide and a base, preferably an amine base such as pyridine in a protic solvent such as tertiary butyl alcohol at reflux temperature for about 6 to about 24 hours. The acetate protecting group is then removed as described above.

The Formula IX compounds wherein the steroid moiety $R^4$ is (B), $Q^2$, $Q^4$ and $Q^5$ are methyiene and $Q^3$ is carbonyl are commercially available from the Sigma Chemical Co., St. Louis, Mo.

The Formula IX compounds wherein the steroid moiety $R^4$ is (B), $Q^2$ and $Q^3$ are taken together to form

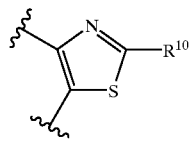

and $Q^4$ and $Q^5$ are methylene are prepared from the corresponding Formula IX compounds wherein $Q^2$ is carbonyl and $Q^3$ is methylene. Thus the appropriate Formula IX compound is brominated by reaction with copper (II) bromide in a polar protic solvent such as methanol at reflux temperature for about 12 hours to about 48 hours. This bromide is treated with a thioamide such as thioacetamide in an anhydrous aprotic solvent such as toluene at reflux temperature for about 12 to about 48 hours. The crude product is treated with an acid, such as p-toluene sulfonic acid in a non-polar aprotic solvent such as toluene at reflux temperature for about 12 to about 24 hours.

The Formula IX compounds wherein the steroid moiety $R^4$ is (B), $Q^2$ is $-CH(CH(CH_3)-CH_2-CH_2-C(=O)(OR^9))-$, $Q^3$ and $Q^5$ are methylene, $Q^4$ is $C=O$ are prepared from the corresponding Formula IX compounds wherein $Q^2$ is $-CH(CH(CH_3)-CH_2-CH_2-C(=O)(OR^9))-$, $Q^3$ is methylene, $Q^4$ is

$Q^5$ is methylene, the $C^3$ hydroxyl group is alpha and the $C^5$ hydrogen is beta. Thus, the two hydroxyl groups are converted to ketones by treatment with an oxidizing agent such as pyridinium chlorochromate in an anhydrous halogenated solvent such as dichloromethane at 0° C. for about 5 to about 15 minutes followed by warming to ambient temperature for about 2 hours to about 6 hours. The $C^3$ ketone can be reduced in the presence of the $C^{12}$ ketone and the configuration at $C^3$ can be controlled by the choice of reducing agents. In the preferred method, treatment of the diketone with a bulky reducing agent such as K-Selectride® reducing agent in an anhydrous aprotic solvent such as tetrahydrofuran at −78° C. for about 5 hours to about 10 hours affords the $C^3$ alcohol in the beta position. Alternatively, if the reduction is carried out using sodium borohydride, in an alcohol solvent such as ethanol, the $C^3$-alpha alcohol is obtained.

The Formula IX compounds wherein the steroid moiety $R^4$ is (B), $Q^2$ is $-CH(CH(CH_3)-CH_2-CH_2-C(=O)(OR^9))-$, $Q^5$ is carbonyl and $Q^3$ and $Q^4$ are methylene are prepared from the corresponding Formula IX compounds wherein $Q^4$ is carbonyl and $Q^5$ is methylene by a carbonyl transposition. This transformation is well known in the literature (see Seebeck, E.; Reichstein, T. Helv. Chim. Acta 26,536 (1943)).

The compounds of Formula I which have been obtained and have asymmetric carbon atoms (e.g., substituents which are introduced onto the structural formula (I) and substructural formula (A) and (B), such as some of the components of the carbamoyl moieties such as substituted amino groups) can be separated into their diastereomers and enantiomers on the basis of their physical chemical differences or optical qualities by methods known per se, for example, by chromatography and/or fractional crystallization. All such isomers, including diastereomers and enantiomers are considered as part of this invention.

The compounds of this invention where $R^5$ contains an amine group are basic and they form acid addition salts. All such acid addition salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, many of the compounds of this invention may be isolated as hydrates and all such hydrates are considered part of this invention.

The compounds of this invention are potent inhibitors of cholesterol absorption and thus are all adapted to therapeutic use as hypercholesterolemia controlling agents in mammals, particularly humans. Since hypercholesterolemia is closely related to the development of generalized cardiovascular, cerebral vascular or peripheral vascular disorders, secondarily these compounds prevent the development of atherosclerosis.

The hypercholesterolemia controlling activity of these compounds may be demonstrated by methods based on standard procedures. For example, the in vivo activity of these compounds in inhibiting intestinal absorption of cholesterol may be determined by the procedure of Melchoir and Harwell (J. Lipid Res., 1985, 26, 306–315).

Activity can be determined by the amount of hypocholesterolemic agent that reduces the cholesterol absorption, relative to the control, in male golden Syrian hamsters. Male golden Syrian hamsters are administered a diet supplemented with 1% cholesterol and 0.5% cholic acid for 4 days. The following day the animals are fasted for 18 hours, then administered a 0.5 ml/100 gm oral bolus of water containing 0.225% methylcellulose, 0.54% Tween™ 80 and 10% ethanol (control vehicle) or an oral bolus that contains, in addition, the desired concentration of the compound to be tested. Immediately following bolus administration, all animals receive a second 1.5 ml oral bolus of liquid hamster diet containing 1% [$^3$H] cholesterol (2.0 µCi/animal; 210 dpm/nmol) and 0.5% cholic acid, and are fasted for an additional 24 hours. At the end of this second fasting period animals are euthanized, livers are excised, saponified and aliquots are decolorized by addition of hydrogen peroxide, neutralized by the addition of 3N HCl and assessed for radioactivity using a liquid scintillation counter. Total hepatic radioactivity is calculated based on measured liver weights. The degree of cholesterol absorption is the amount of labeled cholesterol in the liver of the animals expressed as a percentage of the total radioactivity administered in the oral bolus. The degree to which these compounds inhibit cholesterol absorption is calculated by comparing the percent cholesterol absorption in the treated hamsters to that in the hamsters receiving the vehicle control.

Anti-atherosclerosis effects of the compounds can be determined by the amount of agent that reduces the lipid deposition in the rabbit aorta. Male New Zealand White rabbits are fed a diet containing 0.4% cholesterol and 5% peanut oil for 4 days (meal-fed once per day). Rabbits are bled from the marginal ear vein and total plasma cholesterol values are determined from these samples. The rabbits are then assigned to treatment groups so that each group has a similar mean ± s.d. for total plasma cholesterol concentration. After group assignment, rabbits are dosed daily with compound given as a dietary admix or on a small piece of gelatin based confection. Control rabbits receive only the dosing vehicle be it the food or the gelatin confection.

The cholesterol/peanut oil diet is continued along with the compound administration throughout the study. Plasma cholesterol values can be determined at any point during the study by obtaining blood from the marginal ear vein. After 5 months, the rabbits are sacrificed and the aortae are removed from the thoracic arch to the branch of the iliac arteries. The aortae are cleaned of adventitia, opened longitudinally and then stained with Sudan IV as described by Holman et al. (Lab. Invest. 1958, 7, 42–47). The percent of the surface area stained is quantitated by densitometry using an Optimas Image Analyzing System (Image Processing Systems). Reduced lipid deposition is indicated by a reduction in the percent surface area stained in the drug group in comparison with the control rabbits.

Administration of the compounds of this invention can be via any method which delivers the compounds to the intestinal lumen. These methods include oral routes, intraduodenal routes etc.

The amount of steroidal glycoside administered will, of course, be dependent on the subject being treated, on the severity of the affliction, on the manner of administration and on the judgment of the prescribing physician. However, an effective dosage is in the range of 0.005 to 50 mg/kg/day, preferably 0.01 to 20 mg/kg/day, most preferably 0.01 to 5 mg/kg/day. For an average 70 kg human, this would amount to 0.00035 to 3.5 g/day, preferably 0.0007 to 1.4 g/day, most preferably 0.0007 to 0.35 g/day. In one mode of administration, the compounds of this invention are taken with meals.

For oral administration, which is preferred, a pharmaceutical composition can take the form of solutions, suspensions, tablets, pills, capsules, powders, sustained release formulations and the like.

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages.

The pharmaceutical compositions will include a conventional pharmaceutical carrier or excipient and a compound according to the invention as an active ingredient. In addition, it may include other medicinal or pharmaceutical agents, carriers, adjuvants, etc.

Pharmaceutical compositions according to the invention may contain 0.1%–95% of the compound, preferably 1%–70%. In any event, the composition or formulation to be administered will contain a quantity of a compound according to the invention in an amount effective to alleviate the signs of the subject being treated, i.e., hypercholesterolemia or atherosclerosis.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like.

Liquid pharmaceutically administrable compositions can be prepared by dissolving or dispersing, or otherwise preparing a compound according to this invention and mixing it optionally with a pharmaceutical adjuvant in a carrier, such as, for example, water, saline, aqueous dextrose, glycerol, ethanol, and the like, to thereby form a solution or suspension.

Methods of preparing various pharmaceutical compositions with a certain amount of active ingredient are known, or will be apparent, to those of ordinary skill in this art. For examples, see *Remington's Pharmaceutical Sciences*, Mack Publishing Company, Easter, Pa., 15th Edition (1975).

It should be understood that this invention is not limited to the particular embodiments shown and described herein, but that various changes and modifications may be made without departing from the spirit and scope of this novel concept as defined by the following claims.

EXAMPLE 1

(3β,5α)-3-[(4",6"-Bis-O-[2-fluorophenyl-carbamoyl]-β-D-cellobiosyl)oxy]-androstan-17-one Deacetylation Using Potassium Cyanide Potassium cyanide (24 mg) was added to a solution of (3β,5α)-3-[(4",6"-bis-O-[2-fluorophenyl-carbamoyl]2',2", 3',3",6'-penta-O-acetyl-β-D-cellobiosyl)oxy]-androstan-17-one (0.63 g, 0.57 mmol) in tetrahydrofuran (3 mL) and methanol (3 mL). The reaction was stirred for about 3 hours at room temperature under nitrogen atmosphere. The mixture was concentrated in vacuo and the product precipitated with methanol-water.

The crude material was purified via flash chromatography (95% dichloromethane: 5% methanol). The isolated product was concentrated in vacuo to partial dryness and water was added causing a precipitate to form. The precipitated product was filtered, washed with water and oven-dried to afford 165 mg (33% yield) of the title compound.

m.p. 168–169° C.; FAB MS 911(M+Na)$^+$; Analysis calc. for $C_{45}H_{58}F_2N_2O_{14}$: Calc. C, 56.99; H, 6.87; N, 2.95. Found C, 56.96; H, 6.76; N, 2.91.

In an analogous manner, the following compounds, Examples 2–3, were prepared from the appropriate starting materials using the above general procedure of Example 1.

EXAMPLE 2

(3β,5β)-3-[(4",6"-Bis-O-(2-fluorophenyl carbamoyl)-β-D-cellobiosyl)oxy]-5-cholan-12-on-24-oic acid methyl ester m.p.>265° C.; 1025(M+Na)$^+$; $C_{51}H_{68}F_2N_2O_{16}$.

EXAMPLE 3

(3β,5α,25R)-3-[4",6"-Bis-O-(2-fluorophenyl carbamoyl)-β-D-cellobiosyl-oxy]-12a-homoaza-spirostan-12-one m.p. 192–194° C.; 1066(M+Na)$^+$; $C_{53}H_{71}F_2N_3O_{16}$+4.3 $H_2O$: Calc. C, 56.76; H, 7.15; N, 3.75. Found C, 56.56; H, 6.85; N, 3.56.

EXAMPLE 4

(3β,5α)-3-[(6',6"-Bis-O-[2-fluorophenyl-carbamoyl]-β-D-cellobiosyl)oxy]-androstan-17-one

Carbamoylation

A mixture of (3β,5α)-3-[(β-D-celobiosyl)oxy]-androstan-17-one (0.40 g, 0.65 mmol), pyridine (5 mL) and 4 Å molecular sieves (0.50 g) was stirred for about 10 minutes at room temperature under nitrogen atmosphere. The reaction was then cooled to about −40° C. and 2-fluorophenyl isocyanate (0.12 mL, 1.07 mmol) was added. The reaction mixture was gradually warmed to room temperature and stirred for about 3 hours. The reaction was quenched with methanol. The quenched mixture was concentrated in vacuo twice with toluene in order to remove the pyridine. The crude material was purified via flash chromatography (2% to 10% methanol: dichloromethane). The higher $R_f$ product was concentrated in vacuo, triturated with methanol/water, filtered and washed with water to afford 80 mg (16% yield) of the title compound. m.p. 171–173° C.; FAB MS 911 (M+Na)$^+$; Analysis calc for $C_{45}H_{58}F_2N_2O_{14}$+3 $H_2O$: Calc. C, 57.32; H, 6.84; N, 2.97. Found C, 57.41; H, 6.67; N, 2.83.

EXAMPLE 5

(3β,5α)-3-[(6"-O-[2-Fluorophenyl-carbamoyl]-β-D-cellobiosyl)oxy]-androstan-17-one Further eluting the column of Example 4 above gave a second product which was isolated as before to give 70 mg of the title compound (14%).

m.p. 202–206° C.; FAB MS 774 (M+Na)$^+$; Analysis calc. for: $C_{38}H_{54}FNO_{13}$+3.7 $H_2O$: C, 55.76; H, 7.56; N, 1.71; Found: C, 55.80; H, 7.25; N, 1.68.

In an analogous manner, the following compounds, Examples 6–8, were prepared from the appropriate starting materials using the general procedure described in Example 4.

EXAMPLE 6

(3β,5β)-3-[(6"-O-(2-fluorophenyl carbamoyl)-β-D-cellobiosyl)oxy]5-cholan12-on24-oic acid methyl ester m.p. 152–156° C.; 888 (M+Na)$^+$; Analysis calc. for: $C_{44}H_{64}FNO_{15}$+2 $H_2O$; Calc. C, 58.59; H, 7.60; N, 1.55. Found C, 58.56; H, 7.63; N, 1.65.

EXAMPLE 7

(3β,5α,25R)-3-[(6"-O-(2-Fluorophenyl carbamoyl)-β-D-cellobiosyl)oxy]-12,12-difluoro spirostane m.p. 227–229° C.; 936 (M+Na)$^+$; Analysis calc. for: $C_{46}H_{66}F_3NO_{14}$+2 $H_2O$: 58.16; H, 7.43; N, 1.47. Found: C, 58.28; H, 7.60; N, 1.68.

EXAMPLE 8

(3β,5α,25R)-3-[(6"-O-(2-Fluorophenyl carbamoyl)-β-D-cellobiosyl)oxy]-spirost-9-en-12-one m.p. 176–180° C.; 912(M+Na)$^+$; Analysis calc. for: $C_{46}H_{64}FNO_{15}$+3.3 $H_2O$: Calc. C 58.19; H, 7.49; N, 1.48. Found: C, 58.18; H, 7.39; N, 1.58.

EXAMPLE 9

(3β,5α)-3-[(β-D-Cellobiosyl)oxy]-androstan-17-one

Sodium Methoxide Deprotection

Sodium methoxide (2 g, 0.03 mmol) was added to a solution of (3β,5α)-3-[(hepta-O-acetyl-β-D-cellobiosyl)oxy]-androstan-17-one (27 g, 0.03 mmol) in THF (30 mL) and methanol (60 mL). The mixture was heated to about 50° C. for about 1.5 hours, was cooled and concentrated in vacuo. The residue was triturated with methanol/water and the precipitate was collected, washed with water and dried to afford 18.2 g of the title product as a colorless solid.

m.p.>220° C.; FAB MS 637 (M+Na)$^+$.

In an analogous manner, the following compounds, Examples 10–22, were prepared from the appropriate starting materials using the above general procedure of Example 9.

EXAMPLE 10

(3β)-3-[(β-D-Cellobiosyl)oxy]-androst-5-en-17-one m.p.>200° C.; MS 635 (M+Na)$^+$; $C_{31}H_{48}O_{12}$. Analysis calc. for $C_{31}H_{48}O_{12}$+1.3 $H_2O$ Calc.: C, 58.53; H, 8.02. Found: C, 58.84; H, 8.41.

EXAMPLE 11

(3β,5α)-3[(β-D-Cellobiosyl)oxy]-androstan-16-one m.p.>240° C.; MS 615 (M+H)$^+$; $C_{31}H_{50}O_{12}$.

EXAMPLE 12

2-Methyl-4,5-[(3β,5α)-3-[(β-D-cellobiosyl)oxy]-androstano-[17,16-d]-thiazole m.p.>200° C.; MS 635 (M+Na)$^+$; Analysis calc. for: $C_{31}H_{48}O_{12}$+$H_2O$; Calc. C, 60.41; H, 7.83; N, 4.94. Found C, 60.31; H, 8.04; N, 4.88.

EXAMPLE 13

(3β,5α)-3-[(β-D-Cellobiosyl)oxy]-16-propylenedioxy-androstane m.p.>200° C.; MS 673 (M+H)$^+$; $C_{34}H_{58}O_{13}$.

EXAMPLE 14

((3⊖,5β)-3-[(β-D-Cellobiosyl)oxy]-5-cholan-12-on-24-oic acid methyl ester m.p.>240° C.; MS 751 (M+Na)$^+$; Analysis calc. for $C_{37}H_{60}O_{14}$+2 $H_2O$: Calc. C, 58.09; H, 8.44. Found: C, 58.36; H, 8.49.

EXAMPLE 15

(3β,5α,12β,25R)-3-[(β-D-Cellobiosyl)oxy]12-trifluoroacetamido spirostane m.p.>240° C.; MS 852 (M+H)$^+$; Analysis calc. for $C_{41}H_{64}F_3NO_{14}$+1.5 $H_2O$: Calc. C, 56.03; H, 7.68; N, 1.59. Found: C, 56.10; H, 7.53; N, 1.63.

EXAMPLE 16

(3β,5α,25R)-3-[(β-D-Cellobiosyl)oxy]-12-propylenedioxy-spirostane m.p.>250° C.; MS 835 (M+Na)$^+$; Analysis calc. for $C_{42}H_{68}O_{15}$+2.5 $H_2O$: Calc C, 58.80; H, 8.58. Found: C, 58.89; H, 8.81.

EXAMPLE 17

(3,β5a,25R)-3-[(β-D-Cellobiosyl)oxy]-12-ethylenedioxy-spirostane m.p.>250° C.; MS 821 (M+Na)$^+$; Analysis calc. for $C_{41}H_{66}O_{15}$+1.5 $H_2O$: Calc. C, 59.66; H, 8.43. Found: C, 60.00; H, 8.20.

EXAMPLE 18

(3β,5α)-3-[(β-D-Cellobiosyl)oxy]-androstan-17-benzyl oxime m.p.>250° C.; MS 742 (M+Na)+; Analysis calc. for $C_{38}H_{57}NO_{12}+1H_2O$: Calc. C, 61.86; H, 8.06; N, 1.90. Found: C, 62.01; H, 8.20; N, 1.97.

EXAMPLE 19

(3β,5α,25R)-3-[(β-D-Cellobiosyl)oxy]-12a-homoaza-spirostane-12-one m.p.>250° C.; MS 792 (M+Na)+; Analysis calc. for $C_{39}H_{63}O_{14}+2.2 H_2O$: Calc. C, 57.86; H, 8.39; N, 1.73. Found: C, 57.64; H, 8.30; N, 1.71.

EXAMPLE 20

(3β,5α,25R)-3-[(β-D-Cellobiosyl)oxy]-spirost-9-en-12-one m.p.>250° C.; MS 775 (M+Na)+; Analysis calc. for $C_{39}H_{60}O_{14}+2 H_2O$: Calc. C, 59.38; H, 8.18. Found: C, 59.28; H, 8.23.

EXAMPLE 21

(3β,5α)-3-[(β-D-Lactosyl)oxy]-androstan-17-one m.p.>240° C.; MS 637 (M+Na)+; Analysis calc. for $C_{31}H_{50}O_{12}+1.75 H_2O$: Calc. C, 57.62; H, 8.34. Found: C, 57.66; H, 8.38.

EXAMPLE 22

(3β,5α,25R)-3-[(β-D-Cellobiosyl)oxy]-12,12-difluoro-spirostane m.p.>250° C.; MS 777 (M+H)+; Analysis calc. for $C_{39}H_{62}F_2O_{13}+3.5 H_2O$: Calc C, 55.83; H, 8.29. Found: C, 55.90; H, 8.32.

Preparation A1

(3β,5α)-3-[(4",6"-bis-O-[2-Fluorophenyl-carbamoyl]-2',2",3',3",6'-penta-O-acetyl-β-D-cellobiosyl)oxy]-androstan-17-one

Carbamoylation

A mixture of (3β,5α)-3-[(2',2",3',3",6'-penta-O-acetyl-β-D-cellobiosyl)oxy]-androstan-17-one (0.50 g, 0.61 mmol), methylene chloride (4 mL), triethylamine (0.68 mL, 4.85 mmol) and diethylaminopyridine (0.10 g) was cooled to about 0° C. under nitrogen atmosphere. 2-Fluorophenyl isocyanate (0.37 mL, 3.3 mmol) was added and the reaction was stirred at about 0° C. for about 15 minutes, then at room temperature for about 50 minutes. The reaction was quenched with methanol and diluted with ethyl acetate, washed with water (1×), 1N HCl solution (3×), saturated sodium bicarbonate solution (2×) and brine (1×), dried over sodium sulfate, filtered and concentrated in vacuo. The residual material was triturated with hexanes, filtered, washed with hexanes and dried to afford 600 mg of the titled compound (93%).

FAB MS 1121 (M+H)+.

In an analogous manner, the following compounds, Preparations A2–A3, were prepared from the appropriate starting materials using the above general procedure of preparation A1.

Preparation A2

(3β,5β)-3-[(4",6"-Bis-O-(2-fluorophenyl carbamoyl) 2',2",3',3",6'-penta-O-acetyl-β-D-cellobiosyl)oxy]-5-cholan-12-on-24-oic acid methyl ester

Preparation A3

(3β,5α,25R)-3-[(4",6"-Bis-O-(2-fluorophenyl carbamoyl)2',2",3',3",6'penta-O-acetyl-β-D-cellobiosyl)-oxy]-12a-homoaza-spirostan-12-one

Preparation B1

(3β,5α)-3-[(2',2",3',3",6'-Penta-O-acetyl-β-D-cellobiosyl)oxy]-androstan-17-one

Benzylidene Hydrolysis

Trifluoroacetic acid (1 mL) was added to a solution of (3β,5α)-3-[(4",6"-O-benzylidene2',2",3',3",6'-penta-O-acetyl-β-D-cellobiosyl)oxy]-androstan-17-one (1.47 g, 1.56 mmol) in dichloromethane (10 mL) and methanol (2 mL). The reaction was stirred at room temperature for about 4 hours. The mixture was diluted with ethyl acetate, then washed with water (1×), saturated sodium bicarbonate solution (1×), water (1×) and brine (1×). The organic layer was dried over sodium sulfate, filtered and concentrated in vacuo. The residual material was triturated with hexanes, filtered, washed with hexanes and dried to afford 1.15 g (89% yield) of product.

MS: 847 (M+Na)+.

In an analogous manner, the following compounds, Preparations B2–B3, were prepared from the appropriate starting materials using the above general procedure of preparation B1.

Preparation B2

(3β,5β)-3-[2',2",3',3",6'-Penta-O-acetyl-β-D-cellobiosyl oxy]-5-cholan-12-on-24-oic acid methyl ester

Preparation B3

(3β,5α,25R)-3-[2',2",3',3",6'-Penta-O-acetyl-β-D-cellobiosyl-oxy]-12a-homoaza spirostan-12-one

Preparation C1

(3β,5α)-3-[(4",6"-O-benzylidene-2',2",3',3",6'-penta-O-acetyl-β-D-cellobiosyl)oxy]-androstan-17-one

Benzylidene Formation and Acetylation

A mixture of (3β,5α)-3-[(β-D-cellobiosyl)oxy]-androstan-17-one (3.00 g, 4.88 mmol), camphorsulphonic acid (0.25 g), dichloroethane (90 mL) and paramethoxy-benzaldehyde dimethyl acetal (3.32 mL) was heated to reflux temperature under nitrogen atmosphere. The reaction was stirred at reflux temperature for about 6 hours, at which time formation of the benzylidene was complete. The reaction was cooled in an ice bath and pyridine (11.84 mL, 0.146 mol), dimethylaminopyridine (0.5 g) and acetic anhydride (14.2 mL, 0.15 mol) were added. The reaction was warmed to room temperature and stirred overnight. The reaction mixture was washed with 1N HCl solution (3×), water (1×) and brine (1×). The organic layer was then dried over sodium sulfate, filtered and concentrated in vacuo. The residual material was triturated with hexanes, filtered, washed with hexanes and dried to afford 2.5 g (54% yield) of the title product.

$^1$H NMR (250 MHz, CDCl$_3$): δ 7.38 (d, 2H, J=7 Hz); 6.9 (d, 2H, J=7 Hz); 4.94 (s, 1H); 5.25 (dd, 1H, J=8.0, 7.0 Hz); 5.17 (dd, 1H, J=8.0, 7.0 Hz); 4.92 (dd, 1H, J=6.5, 6.0 Hz); 3.98 (dd, 1H, J=11.0, 2.0 Hz); 4.35 (dd, 1H, J=7.0, 4.0 Hz); 4.07 (dd, 1H, J=11.0, 4.0 Hz); 3.8 (s, 3H); 3.8–3.4 (m, 9H); 2.42 (dd, 1H, J=16.0, 8.5 Hz); 2.1 (s, 3H); 2.03 (s, 3H); 2.02 (s, 3H); 2.0 (s, 6H); 2.0–0.9 (m, 21H); 0.75 (s, 3H); 0.7 (s, 3H).

In an analogous manner, the following compounds, Preparations C2–C3, were prepared from the appropriate starting materials using the above general procedure of Preparation C1.

Preparation C2

(3β,5β)-3-[(4",6"-O-Benzylidene-2',2",3',3",6'-penta-O-acetyl-β-D-cellobiosyl)-oxy]-5cholan-12-on-24-oic acid methyl ester

Preparation C3

(3β,5α,25R)-3-[(4",6"-O-Benzylidene-2',2",3',3",6'-penta-O-acetyl-β-D-cellobiosyl)-oxy]-12a-homoaza-spirostan-12-one

Preparation D1

(3β,5α,25R)-3-[(Hepta-O-acetyl-β-D-cellobiosyl)oxy]12a-homoazaspirostan-12-one

Beckmann Rearrangement

A) A mixture of (3β,5α,25R)-3-[(hepta-O-acetyl-β-D-cellobiosyl)oxy]spirostan-12-one (10.00 g, 9.5 mmol), tetrahydrofuran (50 mL), methanol (50 mL), pyridine (3.08 mL, 38 mmol) and NH$_2$OH.HCl (1.99 g, 28.6 mmol) was stirred at room temperature overnight. The reaction mixture was concentrated in vacuo. The residue was dissolved in ethyl acetate, then washed with 6M HCl (3×) and brine (1×), dried over sodium sulfate, filtered and concentrated in vacuo. Methanol was then added, causing a precipitate to form. The mixture was then concentrated and more methanol was added. After one more concentration, water was added, causing a precipitate to form. The precipitate was filtered, washed with water/methanol and oven-dried.

FAB MS 1064 (M+H)$^+$.

B) Tosyl chloride (0.86 g, 4.5 mmol) was added to a mixture of the product from step A above (1.25 g, 1.17 mmol), pyridine (30 mL) and dimethylaminopyridine (1.00 g). The reaction was stirred overnight. At this point more tosyl chloride (0.41 g) was added and the reaction was again stirred overnight. Upon completion, the reaction was diluted with chloroform, washed with 1N HCl (3×) and brine (1×), dried over sodium sulfate, filtered and concentrated in vacuo to afford 1.24 g (100%) of the product as a foam.

FAB MS 1064 (M+H)$^+$.

Preparation E1

(3β,5α)-3-[(Hepta-O-acetyl-β-D-cellobiosyl)oxy]-androstan-17-(O-benzyl)oxime

Oxime Formation

A mixture of (3β,5α)-3-[(hepta-O-acetyl-β-D-cellobiosyl)oxy]-androstan-17-one (2.00 g, 6.94 mmol), methanol (40 mL), pyridine (1.68 mL, 20.8 mmol) and benzylhydroxylamine hydrochloride was stirred at room temperature for about 1.5 hours. Upon completion, the reaction mixture was concentrated in vacuo. The residue was dissolved in ethyl acetate, washed with water (1×), 0.1 M hydrochloric acid (1×) and brine (1×), dried over sodium sulfate, filtered and concentrated in vacuo to afford 2.74 g (100%) of the title product.

FAB MS 1014 (M+H)$^+$.

Preparation F1

(3β,5α)-3-[(hepta-O-acetyl-β-D-cellobiosyl)oxy]-androstan-17-one

Zinc Fluoride Promoted Glycosidation

Zinc fluoride (14.23 g, 0.138 mol) was added to a suspension of (3β,5α)-3-hydroxy-androstan-17-one (10.0 g, 0.344 mmol) in acetonitrile (500 mL). 20 mL of solvent was distilled off and heptaacetylcellobiosyl bromide (42 g, 0.0603 mol) was added. After about 4 hours at a gentle reflux, the reaction was judged complete by thin layer chromatography. The mixture was filtered through Celite® filter aid and concentrated in vacuo. The crude product was purified by flash chromatography (20% to 30% ethyl acetate/methylene chloride) to afford 31 g of the title product.

$^1$H NMR (250 MHz, CDCl$_3$): δ 5.18 (dd, 1H, J=8.0, 7.0 Hz); 5.15 (dd, 1H, J=8.5, 8.0 Hz); 5.05 (dd, 1H, J=9.0, 8.0 Hz); 4.9 (dd, 1H, J=7.5, 7.0 Hz); 4.85 (dd, 1H, J=7.5, 7.0 Hz); 4.5 (m, 4H); 4.35 (dd, 1H, J=9.0, 4.0 Hz); 4.07 (dd, 1H, J=8.5, 4.0 Hz); 4.02 (dd, 1H, J=10, 2.0 Hz); 3.72 (dd, 1H, J=8.5, 7.5 Hz); 3.55 (m, 3H); 2.45 (dd, 1H, J=16, 8.5 Hz); 2.1 (s, 3H); 2.08 (s, 3H); 2.02 (s, 9H); 2.01 (s, 6H); 1.98 (s, 3H); 1.98–0.9; (m, 20H); 0.85 (s, 3H); 0.8 (s, 3H).

In an analogous manner, the following compounds, Preparations F2–F10, were prepared from the appropriate starting materials using the above general procedure of Preparation F1.

Preparation F2

(3β)-3-[(Hepta-O-acetyl-β-D-cellobiosyl)oxy]-androst-5-en-17-one

Preparation F3

(3β,5α)-3-[(Hepta-O-acetyl-β-D-cellobiosyl)oxy]-androstan-16-one

Preparation F4

2-Methyl-4,5-[(3β,5α)-3-[(hepta-O-acetyl-β-D-cellobiosyl)oxy]]-androstano-[17,16-d]-thiazole

Preparation F5

(3β,5β)-3-[(Hepta-O-acetyl-β-D-cellobiosyl)oxy]-5-cholan-12-on-24-oic acid methyl ester

Preparation F6

(3β,5α,25R)-3-[(Hepta-O-acetyl-β-D-cellobiosyl)oxy]-spirost-9-en-12-one

Preparation F7

(3β,5α)-3-[(Hepta-O-acetyl-β-D-lactosyl)oxy]-androstan-17-one

Preparation F8

(3β,5α,25R)-3-[(Hepta-O-acetyl-β-D-cellobiosyl)oxy]-12,12-difluoro-spirostane

Preparation F9

(3β,5α,25R)-3-[(Hepta-O-acetyl-β-D-cellobiosyl)oxy]-spirostan-12-one

Preparation F10

(3β,5α,25R)-3-[(Hepta-O-acetyl-β-D-cellobiosyl)oxy]-12-trifluoroacetamido spirostane

Preparation G1

(3β,5α,25R)-3-[(Hepta-O-acetyl-β-D-cellobiosyl)oxy]-12-ethylenedioxy-spirostane

Mercuric Bromide/Mercuric Cyanide Glycosidation

A mixture of (3β,5α,25R)3-trimethylsilyloxyspirostan-12-one-1,2-ethanediol ketal (1.5 g, 2.75 mmol), heptaacetyl cellobiosyl bromide (3.84 g, 5.49 mmol) and powdered 4Å molecular sieves (700 mg) in dichloromethane (25 mL) and acetonitrile (10 mL) was stirred for about 15 minutes at room temperature. To this mixture, mercuric cyanide (2.77 g, 11 mmol) and mercuric bromide (3.95 g, 11 mmol) were added. The reaction was then stirred for about 5 hours at room temperature. The reaction was diluted with ethyl acetate (50 mL) and filtered. The filtrate was washed with 1N hydrochloric acid (2×30 mL) and brine (1×), dried over sodium sulfate, filtered and concentrated in vacuo. The crude product was purified via flash chromatography (30% ethyl acetate/hexanes) to afford 910 mg (30% yield) of the title product as a colorless solid. FAB MS 1107 (M+H)$^+$.

In an analogous manner, the following compounds, Preparations G2–G3, were prepared from the appropriate starting materials using the above general procedure of G1.

Preparation G2

(3β,5α)-3-[(Hepta-O-acetyl-β-D-cellobiosyl)oxy]-16-propylenedioxy-androstane

Preparation G3

(3β,5α,25R)-3-[(Hepta-O-acetyl-β-D-cellobiosyl)oxy]-12-propylenedioxv-spirostane Preparation H1

(3β,5α,25R)-3-Trimethylsilyloxy-12-ethylenedioxyspirostane

Silyation of Spirostanes

Trimethylsilyl trifluoromethanesulfonate (0.9 mL, 4.68 mmol) was added dropwise to a solution of (3β,5α,25R)3-hydroxy-12-ethylenedioxyspirostane (1.48 g, 3.12 mmol) and triethylamine (1.62 mL, 16 mmol) in CH$_2$Cl$_2$ (35 mL) at about 0° C. After about 2.5 hours, the mixture was diluted with ethyl acetate (50 mL) and washed with saturated NaHCO$_3$ solution (2×50 mL) and brine (1×50 mL), dried over sodium sulfate, filtered and concentrated in vacuo to afford 1.59 g of the title product as a colorless solid.

$^1$H NMR (250 MHz, CDCl$_3$): δ 4.35 (q, 1H, J=8.0 Hz); 3.9 (m, 4H); 3.45 (m, 2H); 3.35 (dd, 1H, J=11.0, 10.0 Hz); 2.3 (dd, 1H, J=8.0, 7.0 Hz); 2.0–1.0 (m, 24H); 0.91 (d, 3H, J=7 Hz); 0.89 (s, 3H); 0.8 (s, 3H); 0.78 (d, 3H, J=7 Hz); 0.1 (s, 9H).

In an analogous manner, the following compounds, Preparations H2–H3, were prepared from the appropriate starting materials using the above general procedure of Preparation 1.

Preparation H2

(3β,5α)-3-Trimethylsilvioxy-16-propylenedioxy-androstane

Preparation H3

(3β,5α,25R)-3-Trimethylsilvioxy-12-propylenedioxy-spirostane

Preparation I1

3β-5α-16-Propylenedioxy-androstane

A) A mixture of 3β-androstan-16-one (5.30 g, 18.2 mmol), imidazole (3.16 g, 46.4 mmol), t-butyldiphenylsilyl chloride (3.30 g, 21.9 mmol), DMAP (224 mg) and N,N-dimethylformamide (50 mL) was heated to about 35° C. and stirred overnight. Upon completion, the reaction mixture was concentrated in vacuo, then purified by flash chromatography (10% ethyl acetate/hexanes) to afford 7.15 g (97%) of the title product.

FAB MS 405 (M+H)$^+$.

B) A mixture of 3-(t-butyidiphenylsilyloxy)-androstan-16-one (1.20 g, 2.97 mmol), benzene (70 mL), 1,3-propanediol (2.18 mL, 30.2 mmol) and p-toluenesulfonic acid (19 mg) was refluxed overnight under nitrogen atmosphere. Upon completion, the reaction mixture was washed with saturated sodium bicarbonate solution (1×), and brine (1×), dried over magnesium sulfate, filtered and concentrated in vacuo. The crude product was purified via flash chromatography (30% ethyl acetate/hexanes) to afford 833 mg (61%) of the title product as a white solid.

FAB MS 463 (M+H)$^+$.

Preparation J1

(3β,5α,25R)-12-Trifluoroacetamido spirostane

A) Sodium cyanoborohydride (0.51 g, 8.12 mmol) was added to a stirred suspension of hecogenin (5.00 g, 11.6 mmol) and ammonium acetate (8.94 g, 0.116 mol) in methanol (50 mL). The reaction was stirred overnight at room temperature. The reaction was found to be incomplete, so more sodium cyanoborohydride (0.51 g, 8.12 mmol) was added and the reaction was again stirred overnight. Upon completion, concentrated HCl was added until the pH was<2. Methanol was then removed in vacuo. The residue was taken up in water and extracted with ether (2×). Potassium hydroxide (solid) was added to the aqueous layer until the pH>10. The aqueous layer was then saturated with NaCl and extracted with ether (4×). The combined organic layers were dried over magnesium sulfate and concentrated in vacuo to afford 2.25 g (45%) of the title product as a white solid.

FAB MS 432 (M+H)$^+$.

B) Ethyl trifluoroacetate (0.67 mL) was added to a solution of (3β,5α,12β,25R)-12-amino spirostane (1.94 g, 4.49 mmol), methanol (20 mL) and triethylamine (0.63 mL, 4.49 mmol). The reaction was stirred overnight at room temperature. Upon completion, the reaction mixture was concentrated in vacuo, then purified via flash chromatography (30% ethyl acetate/hexanes) to afford 1.75 g (74%) of the title product as a white solid.

FAB MS 528 (M+H)$^+$.

Preparation K1

(3β,5α,25R)-3-Hydroxy-spirost-9-en-12-one

A) To a solution of hecogenin acetate (1.00 g, 2.11 mmol) in t-butyl alcohol (30 mL), pyridine (2 mL) and SeO$_2$ (0.4685 g, 2.11 mmol) were added. The reaction was refluxed overnight. At this point more SeO$_2$ (0.405 g) and pyridine (2 mL) were added and the reaction was again refluxed overnight. Upon completion, the reaction was cooled, filtered through Celite®, washed with ethyl acetate and chloroform and concentrated in vacuo to partial dryness. Water and a small amount of methanol were added to the residual material and was stirred. The material was filtered, recrystallized from methanol and dried to afford 0.6145 g (62%) of the title product.

FAB MS 471 (M+H)$^+$.

B) Sodium methoxide (67 mg) was added to a solution of (3β,5α,25R)-3-acetoxy-spirost-9-en-12-one (585 mg, 1.24 mmol) in THF (5 mL) and MeOH (5 mL). The mixture was heated to a gentle reflux for about 3 hours, cooled and concentrated in vacuo. The residue was dissolved in ethyl acetate/dichloromethane and washed with water and brine, dried ($Na_2SO_4$) filtered and concentrated.

$^{13}C$ NMR (75 MHz, $d^6$ DMSO): δ 171, 120, 110, 79, 70.5, 67, 60, 53.7, 52.5, 51, 42.56, 42.49, 39.32, 37.82, 36.87, 34.74, 32.52, 31.50, 31.36, 31.24, 30.21, 28.78, 27.65, 18.51, 17.14, 15.08, 13.14.

Preparation L1

(3β,5β)-5-Cholan-12-on-24-oic acid methyl ester

A) A mixture of deoxycholic acid methyl ester (5 g, 12.3 mmol), dichloromethane (250 mL) and Celite® (50 g) was cooled to about 0° C. To this mixture, pyridinium chlorochromate (13.3 g, 61.5 mmol) was added. The reaction mixture was warmed to room temperature and stirred for about 3.5 hours. Upon completion, the reaction was diluted with ether and filtered through a silica gel column, using ether as the eluent. The filtrate was concentrated in vacuo to afford 5.0 g of the product as a white solid.

FAB MS 403 $(M+H)^+$.

B) A solution of 3,12-diketo deoxycholic acid methyl ester (5.00 g, 12 mmol) in tetrahydrofuran (80 mL) was cooled to about −78° C. and 1.0 M K-Selectride® reducing agent (18.63 mL, 19 mmol) was added. The reaction was stirred at about −78° C. for about 5 hours. At this point, more K-Selectride (3.6 mL) was added. Upon completion, the reaction was quenched by the addition of water (2 mL), ethanol (7.5 mL), 15% sodium hydroxide (5 mL), 30% hydrogen peroxide (7.5 mL), anhydrous potassium carbonate, tetrahydrofuran (20 mL) and ether (20 mL). The quenched mixture was transferred to a separatory funnel and the organic layer was washed with 10% $NaHSO_3$ (1×) and brine (1×), dried over sodium sulfate, filtered and concentrated in vacuo. The crude product was purified via flash chromatography (50% ethyl acetate/hexanes) to afford 4.75 g of the title product as a white solid.

FAB MS 405 $(M+H)^+$.

Preparation M1

(3β,5α,25R)-12,12-Difluoro-3-hydroxy-spirostane

A solution of (3β,5α,25R)-3-hydroxy-spirostan-12-one (3.00 g, 6.36 mmol) in dichloroethane (40 mL) was cooled to about 0° C. To this solution, diethylaminosulfurtrifluoride (4.20 mL, 32 mmol) was added. The reaction was gradually warmed to room temperature, then was heated to a gentle reflux and stirred for about 24 hours. The reaction was cooled to about 0° C. and quenched with water. The quenched mixture was then diluted with ethyl acetate, the ethyl acetate layer was separated and washed with water (2×), sodium bicarbonate solution (1×) and brine (1×), dried over sodium sulfate, filtered and concentrated in vacuo. The crude product was then flash chromatographed (50% methylene chloride: 50% hexanes: 1% ether) to afford 1.50 g of the acetate protected product as a white solid. The acetate is cleaved by treatment with sodium methoxide in THF/MeOH at room temperature. The product is isolated by precipitation with water, to afford 600 mg of the title compound.

$^{19}F$ NMR (300 MHz, $CDCl_3$): δ −100 (d, 1F, J=240 Hz); −111 (dd, 1F, J=240, 15 Hz).

Preparation N1

(3β,5α,25R)-3-Hydroxy-12-propylenedioxy-spirostane

Propylene glycol (17.72 mL, 0.24 mol) was added to a solution of hecogenin acetate (2.00 g, 4.23 mmol) in dichloromethane (50 mL). This mixture was allowed to stir until homogeneous, then borontrifluoride etherate (2.76 mL, 22 mmol) was added dropwise. The reaction was stirred under nitrogen at room temperature for about 72 hours. Upon completion, the reaction mixture was poured into a separatory funnel containing ice water and dichloromethane. The organic layer was washed with sodium bicarbonate solution (1×) and brine (1×), dried over sodium sulfate, filtered and concentrated in vacuo to afford 2.27 g of crude material. TLC. showed the presence of two products. The material was flash chromatographed (50% ethyl acetate/hexanes) to isolate the two products. NMR showed the two products to be hecogenin propylene ketal acetate (0.50 g) and hecogenin propylene ketal (1.04 g), FAB MS 531 $(M+H)^+$.

In an analogous manner, the following compound, Preparation N2, was prepared from the appropriate starting materials using the above general procedure of Preparation N1.

Preparation N2

(3β,5α,25R)-3-Hydroxy-12-ethylenedioxy-spirostane

Preparation O1

2-Methyl-4,5-[(3β,5α)-3-hydroxy-androstano-[17,16-d]]-thiazole

A) A mixture of (3β,5═)-3-hydroxy-androstan-17-one (5.00 g, 0.017 mol) and copper (II) bromide (11.68 g, 0.05 mol) in methanol (185 mL) was refluxed under nitrogen for about 24 hours. Upon completion, the reaction mixture was poured into water (250 mL) and the resulting mixture was extracted with chloroform (4×200 mL). The combined extracts were dried over sodium sulfate and evaporated in vacuo to give 8.07 g of white solid. The crude product was purified via flash chromatography (50% ethyl acetate/ hexanes) to afford 6.65 g of the desired product.

Analysis calculated for $C_{19}H_{29}BrO_2$: C, 61.78, H, 7.91. Found C, 58.65, H, 7.38. FAB MS: 369 $(M+H)^+$. m.p. 158–160° C.

B) A solution of (3β,5α)-16-bromo-3-hydroxy-androstan-17-one (2.50 g, 6.77 mmol) and thioacetamide (0.509 g, 6.77 mmol) in toluene (150 mL) was refluxed under nitrogen for about 24 hours. The solid that separated was collected, washed with toluene (25 mL) and dried to afford 2.097 g of a tan solid. The crude product was then dissolved in toluene (100 mL) and p-toluenesulfonic acid (0.05 g) was added. This mixture was refluxed into a Dean-Stark trap for 19 hours. The reaction mixture was then concentrated in vacuo to give a tan solid.

FAB MS 346 $(M+H)^+$.

What is claimed is:

1. A steroidal glycoside compound of Formula I

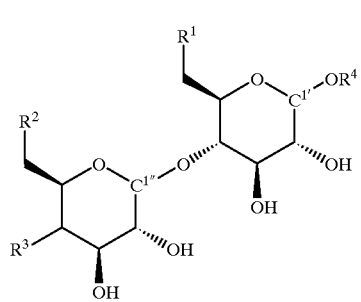

Formula I and the pharmaceutically-acceptable salts and hydrates thereof wherein:

$R^1$, $R^2$ and $R^3$ are each independently hydrogen, hydroxy, halo, amino, azido, $(C_1-C_6)$alkoxy$(C_1-C_6)$alkoxy or $-Z-R^5$;

Z for each occurrence is independently selected from the group consisting of $-NH-C(=O)-$, $-O-C(=O)-$, $-O-C(=O)-N(R^6)-$, $-NH-C(=O)-N(R^6)-$, $-O-C(=S)-N(R^6)-$ and $-O-C(=O)-N-(R^6)-$;

$R^4$ is

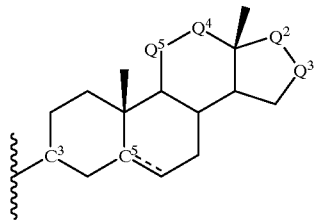

wherein:

- - - - - is optionally a double bond;

$Q^2$ is $-C(=O)-$, $-CH_2-$, $-C(N=OR^9)-$ or $-CH(CH(CH_3)-CH_2-CH_2-C(=O)(OR^9))-$;

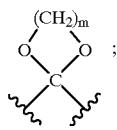

$Q^3$ is $-C(=O)-$, $-CH_2-$ or $Q^4$ is $-CH_2-$ or $-C(=O)-$; and $Q^5$ is $-CH_2-$ or $-C(=O)-$;

$R^5$ for each occurrence is independently aryl, aryl$(C_1-C_6)$alkyl, $(C_2-C_4)$alkenyl, $(C_1-C_6)$alkyl, $(C_3-C_7)$cycloalkyl or $(C_3-C_7)$cycloalkyl$(C_1-C_6)$alkyl, and each $R^5$ may be optionally mono-, di, or tri-substituted independently with halo, $(C_1-C_4)$alkyl, hydroxy, phenoxy, trifluoromethyl, nitro, $(C_1-C_4)$alkoxy, methylenedioxy, oxo, $(C_1-C_4)$alkylsulfanyl, $(C_1-C_4)$alkylsulfinyl, $(C_1-C_4)$alkylsulfonyl, dimethylamino, mono- or di-$(C_1-C_4)$alkylaminocarbonyl, $(C_1-C_4)$alkylcarbonyl, $(C_1-C_4)$alkoxycarbonyl or pyrrolidinylcarbonyl;

$R^6$ for each occurrence is independently hydrogen or $(C_1-C_4)$alkyl, or $R^6$ is taken together with the nitrogen to which it is attached and with $R^5$, wherein $R^5$ is a covalent bond, to form pyrrolidinyl, piperidinyl, N-methylpiperazinyl, indolinyl or morpholinyl, and such cyclic group may be mono-substituted on a carbon atom with $(C_1-C_4)$alkoxycarbonyl;

$R^9$ is $(C_1-C_4)$alkyl or aryl$(C_1-C_6)$alkyl;

m is 2, 3 or 4;

wherein aryl is carbon-linked and is phenyl, furyl, thienyl, pyrrolyl, oxazolyl, isoxazolyl, oxadiazolyl, thiazolyl, isothiazolyl, benzothiazolyl, thiadiazolyl, pyrazolyl, imidazolyl or pyridyl;

provided that where $Q^2$ is $-C(=N-OR^9)-$, $Q^3$ is not $-C(=O)-$.

2. A compound according to claim 1 wherein the $C^3$ oxy is beta, and the $C^5$ hydrogen is alpha.

3. A compound according to claim 2 wherein the $C^{1'}$ and $C^{1''}$ anomeric oxy are beta, and $R^3$ is alpha.

4. A compound according to claim 3 wherein $R^1$ is hydroxy, $R^2$ and $R^3$ are each independently $Z-R^5$ where Z is $-O-(C=O)-N(R^6)-$ and $R^6$ is hydrogen.

5. A method of treating hypercholesterolemia which comprises administering to a mammal in need of such treatment a therapeutically effective amount of a compound of claim 1.

6. A method of treating atherosclerosis which comprises administering to a mammal in need of such treatment a therapeutically effective amount of a compound of claim 1.

7. A pharmaceutical composition for the treatment of hypercholesterolemia or atherosclerosis in a mammal which comprises a compound of claim 1 and a pharmaceutically acceptable carrier.

* * * * *